United States Patent [19]
Domb et al.

[11] Patent Number: 5,227,165
[45] Date of Patent: Jul. 13, 1993

[54] LIPOSPHERE DELIVERY SYSTEMS FOR LOCAL ANESTHETICS

[75] Inventors: Abraham J. Domb; Manoj Maniar, both of Baltimore, Md.

[73] Assignee: Nova Pharmaceutical Corporation, Baltimore, Md.

[21] Appl. No.: 826,218

[22] Filed: Jan. 22, 1992

Related U.S. Application Data

[63] Continuation of Ser. No. 607,543, Nov. 8, 1990, abandoned, which is a continuation-in-part of Ser. No. 435,546, Nov. 13, 1989, abandoned.

[51] Int. Cl.$^5$ .................. A61K 9/127; B01J 13/02
[52] U.S. Cl. ..................................... 424/450; 264/41; 264/43; 264/44; 428/402.2; 428/402.24
[58] Field of Search ................. 424/450; 264/4.1–4.3, 264/4.4; 428/402.2, 402.24

[56] References Cited

U.S. PATENT DOCUMENTS

| | | | |
|---|---|---|---|
| 3,004,892 | 10/1981 | Hainsworth et al. | 167/66 |
| 3,159,545 | 12/1964 | Kidwell et al. | 167/83 |
| 3,159,600 | 12/1964 | Watkins | 260/46.5 |
| 3,804,776 | 4/1974 | Yazawa et al. | 252/316 |
| 3,957,971 | 5/1976 | Oleniacz | 424/70 |
| 3,993,754 | 11/1976 | Rahman et al. | 424/177 |
| 4,010,038 | 3/1977 | Iwasaki et al. | 106/22 |
| 4,025,455 | 5/1977 | Shackle | 252/316 |
| 4,029,762 | 6/1977 | Galanos et al. | 424/87 |
| 4,089,801 | 5/1978 | Schneider | 252/316 |
| 4,145,410 | 3/1979 | Sears | 424/19 |
| 4,168,308 | 9/1979 | Wretlind et al. | 424/244 |

(List continued on next page.)

FOREIGN PATENT DOCUMENTS

| | | |
|---|---|---|
| 0042249 | 12/1981 | European Pat. Off. . |
| 0167825 | 1/1986 | European Pat. Off. . |
| 0177368 | 9/1986 | European Pat. Off. . |
| 0209870 | 1/1987 | European Pat. Off. . |
| 0270460 | 6/1988 | European Pat. Off. . |
| 0274431 | 7/1988 | European Pat. Off. . |
| 2601207A1 | 7/1976 | Fed. Rep. of Germany . |
| WO 83/00294 | 3/1983 | PCT Int'l Appl. . |
| WO A8500011 | 3/1985 | PCT Int'l Appl. . |
| 2135647A | 9/1984 | United Kingdom . |

OTHER PUBLICATIONS

Friedman, et al., *Drug Development and Industrial Pharmacy*, 13 (9–11), 2067–2085 (1987).
Gasco, et al., *Il Farmaco—Ed. Pr.* 43(10) 326 (1987).
Gasco, et al., *International Journal of Cosmetic Science* 10(6), 263–269 (1988).
Kawamata, et al., *J. Pharm. Sci* 76(11), S275, Abstract No. 04-W-19 (1987).
Schmidt, et al., *Acta Pharmaceutical Technologica* 38(1), 34 (1989).
Wang, et al., *J. Pharm. Sci.* 76(11), S305, Abstract No. N 07-W-21 (1987).
Wang et al., *J. Pharm. Sci.* 76(11), S305, Abstract No. N 07-W-22.
Sasaki, et al., *J. Pharm. Dyn.* 7, 120–130 (1984).
Venkatesh, et al., *J. Pharm. Sci.* 76(11), S305, Abstract No. N 07-W-19.
Gao and Huang, *Biochim. Biophys. Acta* 897, 377–383 (1987).

Primary Examiner—Thurman K. Page
Assistant Examiner—G. S. Kishore
Attorney, Agent, or Firm—Kilpatrick & Cody

[57] ABSTRACT

A local anesthetic microsuspension system is disclosed that includes liposheres, that are solid, water-insoluble microparticles that have a layer of a phospholipid embedded on their surface. The core of the liposphere is a solid anesthetic such as lidocaine or marcaine, or an anesthetic dispersed in an inert solid vehicle, such as a wax. Anesthetic liposheres provide a controlled delivery of local anesthetics to achieve extended, effective relief from pain by slowly releasing the anesthetic from the solid hydrophobic core. This is highly preferred over the situation in which an aqueous solution of local anesthetic must be frequently administered because it is quickly systemically absorbed.

29 Claims, 2 Drawing Sheets

U.S. PATENT DOCUMENTS

| | | | |
|---|---|---|---|
| 4,186,183 | 1/1980 | Steck et al. | 424/38 |
| 4,201,767 | 5/1980 | Fullerton et al. | 424/89 |
| 4,224,179 | 9/1980 | Schneider | 252/316 |
| 4,235,871 | 11/1980 | Papahadjopoulos et al. | 424/19 |
| 4,280,996 | 7/1981 | Okamoto et al. | 424/199 |
| 4,298,594 | 11/1981 | Sears et al. | 424/19 |
| 4,310,506 | 1/1982 | Baldeschwieler et al. | 424/1 |
| 4,317,743 | 3/1982 | Chang | 252/316 |
| 4,331,654 | 5/1982 | Morris | 424/38 |
| 4,332,796 | 6/1982 | Los | 424/229 |
| 4,349,529 | 9/1982 | Morcos et al. | 424/1 |
| 4,356,167 | 10/1982 | Kelly | 424/38 |
| 4,377,567 | 3/1983 | Geho | 424/1 |
| 4,404,183 | 9/1983 | Kawata et al. | 424/19 |
| 4,434,153 | 2/1984 | Urquhart et al. | 424/22 |
| 4,438,052 | 3/1984 | Weder et al. | 264/4.6 |
| 4,439,194 | 3/1984 | Harwood et al. | 604/890 |
| 4,446,165 | 5/1984 | Roberts | 426/602 |
| 4,448,765 | 5/1984 | Ash et al. | 424/14 |
| 4,460,560 | 7/1984 | Tokes et al. | 424/1.1 |
| 4,485,054 | 11/1984 | Mezei et al. | 264/4.6 |
| 4,492,720 | 1/1985 | Mosier | 427/213.3 |
| 4,515,736 | 5/1985 | Deamer | 264/4.3 |
| 4,544,545 | 10/1985 | Ryan et al. | 424/1.1 |
| 4,563,354 | 1/1986 | Chang et al. | 424/195.1 |
| 4,610,868 | 9/1986 | Fountain et al. | 424/1.1 |
| 4,622,219 | 11/1986 | Haynes | 424/450 |
| 4,725,442 | 2/1988 | Haynes | 424/490 |
| 4,752,485 | 6/1988 | Sharma et al. | 426/99 |
| 4,761,288 | 8/1988 | Mezel | 424/450 |
| 4,794,000 | 12/1988 | Ecanow | 424/457 |
| 4,797,288 | 1/1989 | Sharma et al. | 424/476 |
| 4,804,548 | 2/1989 | Sharma et al. | 426/96 |
| 4,816,247 | 3/1989 | Desai et al. | 424/80 |
| 4,828,857 | 5/1989 | Sharma et al. | 426/285 |
| 4,880,634 | 11/1989 | Speiser | 424/450 |
| 4,894,233 | 1/1990 | Sharma et al. | 424/440 |
| 4,894,234 | 1/1990 | Sharma et al. | 424/440 |
| 4,911,928 | 3/1990 | Wallach | 424/450 |
| 4,914,084 | 4/1990 | Ecanow | 514/6 |
| 4,929,508 | 5/1990 | Sharma et al. | 424/439 |
| 4,933,183 | 6/1990 | Sharma et al. | 424/439 |
| 4,935,242 | 6/1990 | Sharma et al. | 424/439 |
| 4,963,367 | 10/1990 | Ecanow | 424/485 |
| 4,973,465 | 11/1990 | Baurain et al. | 424/406 |

LIPOSPHERE DELIVERY SYSTEMS FOR LOCAL ANESTHETICS

This application is a continuation of application Ser. No. 07/607,543, filed Nov. 8, 1990 now abandoned, which in turn was a continuation-in-part of Ser. No. 07/435,546, filed Nov. 13, 1989, now abandoned.

BACKGROUND OF THE INVENTION

This invention is in the area of controlled delivery devices for the administration of anesthetics.

Products for the moderation of pain, referred to as analgesics, represent one of the largest markets targeted by pharmaceutical companies. In fact, the market for ethical analgesic products in the United States alone is estimated to reach three billion dollars in 1990 and rise to over four billion dollars by 1995.

Pharmaceutical analgesics include a variety of classes of drugs, such as general anesthetics, non-steroidal anti-inflammatories, and local anesthetics. General anesthetics reduce pain by producing a loss of consciousness. Local anesthetics cause a loss of sensation in a localized area of the body without a loss of consciousness. Non-steroidal anti-inflammatories may ameliorate the pain but do not cause a loss of sensation or consciousness.

Among the general anesthetics are centrally acting narcotics, including morphine, demerol, fentanyl and codeine. These drugs act through opiate receptors in the central nervous system. The major advantage of centrally acting narcotics is the production of profound widespread analgesia for severe pain. These opiates are administered internally, parenterally, or topically. Dosage forms are available that are effective for durations of from 4 to 12 hours. Although centrally acting narcotics are quite effective in mitigating pain, they are associated with serious side effects, including addiction, respiratory depression, apnea, circulatory depression, respiratory arrest, shock and cardiac arrest.

Non-steroidal anti-inflammatory drugs (NSAIDs) include ibuprofen, indomethacin, acetaminophen, piroxicam, naproxen, flufenamic acid and mefenamic acid. The NSAIDs are generally administered orally two to four times daily. They are less potent than the centrally acting narcotics and have a different spectrum of side effects. The major adverse reactions of NSAIDs include gastrointestinal tract ulceration, bleeding and perforation, blurred and/or diminished vision, edema, and prolonged bleeding time.

Local anesthetics block the generation and conduction of nerve impulses by increasing the threshold for electrical excitation in the appropriate nerve, by slowing the propagation of the nerve impulse, and by reducing the rate of rise of the action potential. Local anesthetics are extremely potent and result in a virtually complete loss of sensation in the treated area of the body. Loss of nerve function is generally observed in the following order: pain, temperature, touch, proprioception, and skeletal muscle tone. Commonly used anesthetics include carbocaine, xylocaine, and marcaine.

Local anesthetics are preferred over general anesthetics because of the serious complications that can occur during general anesthesia. However, even local anesthetics, which are usually injected as an aqueous solution, are eventually absorbed from the site of application into the circulation system, and their therapeutic indices, dosages, and frequency of dosage, must therefore be strongly considered before administration to a patient. The more frequently the local anesthetic must be administered, the more likely it is that systemic toxicity will develop.

A local anesthetic must remain active long enough to allow sufficient time for surgery or pain moderation. However, its effectiveness should not last so long that it creates an extended recovery period. There are situations in which local anesthesia lasting for a few days, weeks or even months is desirable. In general, the duration of action of the local anesthetic is proportional to the time during which it has contact with the nerve tissue. Therefore, procedures that maintain the localization of the drug at the nerve greatly prolong the period of anesthesia.

To be efficacious, local anesthetics must have hydrophobic qualities to bind to and cross the cell membrane, yet also have hydrophilic properties to dissolve in water and diffuse to the site of action. The duration of action, which is limited by the fairly rapid process of absorption into the blood, can be increased by decreasing the water solubility of the drug, however, this also decreases the ability to administer the drug in an aqueous injection.

Local anesthetics have been prepared in a number of delivery systems. U.S. Pat. Nos. 4,622,219 and 4,725,442 to Haynes describe a method to administer a liquid general anesthetic such as halothane, isoflurane, enflurane, or methoxyflurane as a local anesthetic, by incorporating the liquid into an unilamellar phospholipid vesicle that consists of a spherical lipid layer surrounding an internal oil phase. U.S. Pat. No. 4,761,288 to Messi describes a multiphase drug delivery system that includes lipid vesicles encapsulating a saturated solution of biologically active compound and biologically active compound in the solid form. European Patent Application No. 88300529.0 filed by Vestar, Inc., describes aqueous emulsions of phospholipid resides at 100 nm or less diameters encapsulating active ingredients and a triglyceride.

Liposomes have also been used for encapsulation of anesthetics. The problems with using liposomes and vesicles as delivery devices are manifold. They are difficult to prepare, unstable, and can only be used for encapsulation of certain types of materials.

It is therefore an object of the present invention to provide a composition and method to locally alleviate pain for an extended period without the need for frequent administration of the drug.

It is a further object of the present invention to provide a composition and method to locally alleviate pain for an extended period without the side effects associated with general anesthetic.

It is another object of the present invention to provide a composition, and method of use thereof, for alleviation of pain, that is easy to prepare and stable for an extended period of time prior to use and in vivo.

SUMMARY OF THE INVENTION

Solid, water-insoluble lipospheres including a solid hydrophobic core formed of a local anesthetic or analgesic, alone or in combination with a carrier, having a layer of a phospholipid embedded on the surface of the core, are disclosed for use in providing extended relief from pain. The core of the liposphere is a solid anesthetic such as lidocaine or marcaine, or an anesthetic dispersed in an inert solid vehicle, such as a wax.

Liposphere can be prepared by: (1) forming a liquid solution or suspension of the anesthetic by either melting the anesthetic to be delivered, or dissolving or dispersing the anesthetic to be delivered in a liquid vehicle to form a liquid anesthetic that solidifies at a temperature above freezing (the melting temperature); (2) adding phospholipid and an aqueous solution to the liquid anesthetic to form a suspension; (3) mixing the suspension at a temperature above the melting temperature until a homogeneous fine preparation is obtained; and then (4) rapidly cooling the suspension to below the melting point of the liquid anesthetic. The liposphere formed by this process have a diameter of greater than one micron coated with a layer of a phospholipid. The hydrophobic side of the phospholipid is embedded in the surface of the solid hydrophobic core and the hydrophilic side of the phospholipid interfaces with the aqueous solution. In the preferred embodiment, the core has a melting temperature of greater than 30° C.

Liposphere can be designed to release drug over a period of several hours to approximately four or five days, or longer, by varying the ratio of carrier to anesthetic in the core, by choice of carrier (for example, poly lactic acid and polycaprolactone release drug over a long period), concentration of formulation and amount of liposphere administered.

DETAILED DESCRIPTION OF THE INVENTION

Figure 1:
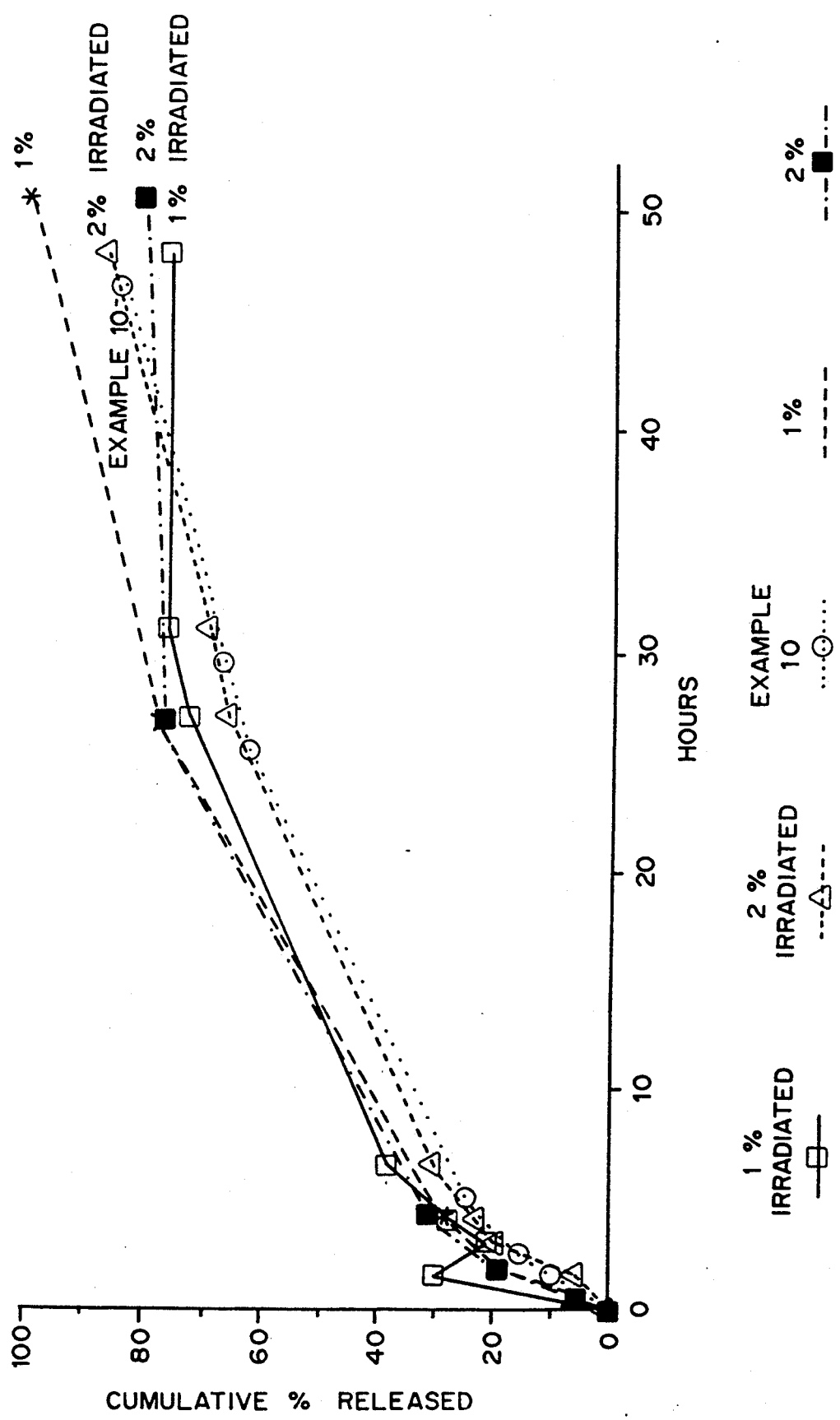
FIG. 1 is graph of the release (cumulative % released) over time (hours) of marcaine from liposphere formed of marcaine:tristearin:phosphatidyl choline, 1:4:2 (-*-), (-square-); and 2:4:2 (-dark square-), (-triangle-), in suspension and after irradiation, respectively. The release of marcaine from liposphere made by sonication (-O-) is also shown.

A delivery system for anesthetics and analgesics is described that results in an extended period of analgesic activity. As used herein, "anesthetic" refers to compounds having localized or general anesthetic activity or analgesic activity. The delivery system are the liposphere described in co-pending U.S. Ser. No. 07/435,546, entitled "Liposphere for Controlled Delivery of Substances," filed on Nov. 13, 1989, by Abraham J. Domb. Many of the side effects resulting from direct administration of the anesthetics are avoided by using the liposphere delivery system.

The liposphere are distinct from microdroplets, vesicles or liposomes since the liposphere have solid inner cores at the temperature at which they are used (usually room temperature or body temperature). The temperature referred to as the "melting temperature" is defined as the temperature at which the solid core material becomes liquid, and the phospholipid coating is entrapped and fixed to the particle surface. The liposphere are distinct from microspheres of uniformly dispersed material in homogenous polymer since they consist of at least two layers, the inner solid particle and the outer layer of phospholipid.

The combination of solid inner core with phospholipid exterior confers several advantages on the liposphere as compared with conventional microspheres and microparticles, including high dispersibility in an aqueous medium, and a release rate for the entrapped substance that is controlled by the phospholipid coating and the carrier. There are also many advantages over other dispersion based delivery systems. Liposphere have increased stability as compared to emulsion based delivery systems, including vesicles and liposomes, and are more effectively dispersed than most suspension based systems. Further, the substance to be delivered does not have to be soluble in the vehicle since it can be dispersed in the solid carrier. Liposphere also have a lower risk of reaction of substance to be delivered with the vehicle than in emulsion systems because the vehicle is a solid inert material. Moreover, the release rate of the substance from the liposphere can be manipulated by altering either or both the inner solid vehicle or the outer phospholipid layer. Liposphere are also easier to prepare than vehicles such as liposphere, and are inherently more stable. Stability has become the major problem limiting the use of liposomes for controlled drug delivery, both in terms of shelf life and after administration to a patient. Liposomes and vesicles do not remain intact or available in vivo for more than a few hours to a couple of days.

Methods of Use of Anesthetic Liposphere

One of the advantages of the liposphere containing anesthetic is that they can provide relief for an extended period of time following a single administration, even with anesthetics normally having very short half-lives. The side effects of general anesthesia are avoided. Further, the patient is not burdened with the disorientation and fatigue that accompanies other means of anesthesia. He can often continue with his daily routine. Another advantage of this delivery system is that a vasoconstrictor is not required to attain prolonged duration of analgesic action.

The liposphere can be used to alleviate the significant discomfort resulting from surgically or trauma induced injuries, including rib and sternum pain associated with thoracic surgery, childbirth, episiotomy, post-surgical incisions, aphthous ulcers, and active herpes lesions, as well as for the control of superficial musculoskeletal pain associated with fractures, dislocations, sprains and strains and the pain associated with dental procedures.

The liposphere can be used to provide the patient with several days of relief from pain resulting from episiotomy by a single injection, rather than several injections of morphine, followed by oral administration of analgesics. This is especially beneficial for women after childbirth, when it is important to minimize the blood levels of drugs during nursing.

The liposphere can be used in place of epidural catheters, for example, during lower abdominal surgery. These catheters are insert immediately prior to surgery and remain in place for four to five days following surgery.

The liposphere can also be used to topically anesthetize the eyes, the skin and mucous membranes.

Current therapies for superficial trauma and musculoskeletal pain due to strains, sprains, dislocations and fractures are of varying effectiveness, and include oral administration of medications such as Percoset, Darvon and Tylenol 3. A single injection of controlled-release analgesic liposphere can provide up to six days of relief.

Pain from aphthous ulcers and active herpes lesions are presently treated with over-the-counter topical analgesic medications, and require frequently repeated applications of product. They can be more efficiently treated by administration of lipospheres in a cream or by injection at the site of the lesion.

Anesthetic Liposphere Compositions

Lipospheres can be mixed with a variety of other pharmaceutically active agents and/or vehicles for topical, enteral or parenteral administration. The lipospheres can include, or be combined with, other pharmaceutically active agents such as antibiotics, antifungals, antivirals, chemotherapeutic agents, or other compounds that would otherwise induce pain. For example, amphotericin B, oil based injectables, and topical creams such as betadine and sulfamefenamide, can be made less painful by administering them in conjunction with anesthetic liposphere. Liposphere formulations in a paste, suspension, or freeze dried formulation can also contain antimicrobial agents or preservatives (such as gentamicin and vancomycin) to reduce the incidence of local bacterial infections associated with lipid-based injections. Examples of stable preservatives, creams, and ointment formulations are listed in Martindale, *The Extra Pharmacopoeia*. The Pharmaceutical Press, 28th Edition (1982). The core material must not be soluble in the vehicle.

The liposphere are administered to the patient topically, enterally (orally, rectally), or parenterally (intravenously, subcutaneously, intramuscularly, intraperitoneally) in the appropriate carrier for administration to the patient. The dosage is determined by the release rate of the anesthetic in combination with the known pharmokinetics of the compound, using standards methods known to those skilled in the art.

The liposphere formulations are stored in aqueous buffer, freeze dried, or in an ointment or cream base, in the freezer, refrigerator or room temperature. It is preferred to store the formulations suspended in an aqueous solution in the refrigerator for immediate use.

Preparation of Liposphere

The preparation and modification of liposphere is described first with reference to the following general descriptions and then with reference to the following non-limiting examples of the preparation and application of liposphere.

Selection of the Solid Core of the Liposphere.

In the preferred embodiment, the liposphere contains a core that has a melting temperature of 30° C. or higher. The core is prepared by choosing an anesthetic to be delivered that has a melting temperature of approximately 30° C., or by mixing the anesthetic to be delivered in a carrier to produce a mixture having a melting point of approximately 30° C. The melting point of the substance to be delivered, alone or in combination with the carrier, should preferably be below 120° C. The substance, or substance and carrier, should also be stable in the liquid form when mixed with hot aqueous media.

The carrier must be compatible with the substance to be delivered. Suitable pharmaceutical solid carriers are inert hydrophobic biocompatible materials with a melting range between 30° and 120° C. Examples are natural, regenerated, or synthetic waxes such as beeswax and carnauba wax; cholesterol; fatty acid esters such as ethyl stearate, isopropyl myristate, and isopropyl palmitate; high molecular weight fatty alcohols such as cetostearyl alcohol, cetyl alcohol, stearyl alcohol, and oleyl alcohol; solid hydrogenated castor and vegetable oils; hard and soft paraffins; hard fat such as tristearin; biodegradable polymers such as polycaprolactone, polyamides, polyanhydrides, polycarbonates, polyorthoesters, polylactic acids, and copolymers of lactic acid and glycolic acid; cellulose derivatives and mixtures thereof. These materials are known to those skilled in the art and most are commercially available, as demonstrated by the extensive list of suitable carrier materials in Martindale, *The Extra Pharmacopoeia*, The Pharmaceutical Press, 28th Edition pp 1063-1072 (1982).

The release rate of the anesthetic from the liposphere is dependent in part upon the composition of the core, as well as the outer phospholipid layer, and can be altered by varying the compositions appropriately.

It is often desireable to deliver a water soluble anesthetic to a targeted area, or to control the release of a water soluble substance. Since the inner core of the liposphere is hydrophobic, it is necessary to decrease the water solubility of the anesthetic before liposphere preparation. Methods to decrease water solubility include using a water insoluble salt or base, complex, or insoluble prodrug; preincorporating the drug into hydrophobic microparticles that can be used as drug particles; or preparing an aqueous medium that the drug is less soluble in, for example, by adjustment of pH or ionic strength, or by adding salts or additives. If the substance to be delivered is rendered less water soluble by adjustment of pH or ionic strength, the resulting liposphere can be isolated by filtration or centrifugation and reconstituted with an appropriate buffer solution prior to use.

Active materials can be preincorporated into microparticles of a hydrophobic solid phase, such as tristearin (melting point 65° C. to 72° C.), that can then be incorporated into liposphere with a vehicle having a lower melting point, such as ethyl stearate (melting point 35° C.), to avoid melting the tristearin particles containing the active material. In this form, the tristearin-active material particles are the hydrophobic "drug" which is dispersed in the ethyl stearate liposphere. The formulations can then be freeze dried with standard techniques and reconstituted prior to use.

Selection of the Phospholipid Coating

The solid core of the liposphere is coated with one or more phospholipids that are embedded into the surface of the solid core during manufacture. Mixtures of two or more phospholipids can be used to vary the surface properties and reactivity of the liposphere.

Phospholipid

A phospholipid is a phosphorylated diacylglyceride molecule or its derivative. The parent structure is diacylglycerol phosphate, or phosphatidic acid. Phosphatidyl choline (lecithin) is the choline ester of phosphorylated diacylglyceride. Synthetic lecithin are available with acyl chain lengths ranging from 4 to 19 carbons. The preferred lecithins for biological applications are those with alkyl chain lengths in the biological range (10 to 18 carbons). Naturally occurring lecithin can be obtained from a variety of sources such as egg, bovine heart, or soy bean. Unsaturated lecithins (dioleoyl; dilinoleoyl; alpha-palmitoyl, beta oleoyl; alpha palmitoyl, beta linoleoyl; and alpha oleoyl, beta palmitoyl), dianachidonyl lecithin (highly unsaturated and a prostaglandin precursor), and alpha palmito beta myristoyl lecithin are also available.

A molecule somewhat structurally related to phosphatidic acid, sphingomyelin, is also suitable for use in the coating of lipospheres.

Certain phospholipids, such as phosphatidic acid, phosphatidyl serine, phosphatidyl inositol, cardiolipin (diphosphatidyl glycerol), and phosphatidyl glycerol, can react with calcium in serum, causing aggregation or the binding of liposperes to cell membranes. These unfavorable reactions can be minimized by combining these phospholipids with non-calcium binding phospholipids such as phosphatidylcholine. Phosphatidic acid can be isolated from egg or prepared synthetically (dimyristoyl, dipalmitoyl and distearoyl derivatives are available from Calbiochem). Bovine phosphatidyl serine is also available commercially (Sigma Chemical Co., St. Louis, Mo.). Phosphatidyl inositol can be isolated from plant or bovine sources. Cardiolipin can be purified from bovine or bacterial sources. Phosphatidyl glycerol can also be purified from bacterial sources or prepared synthetically.

Phosphatidyl ethanolamine in the pure state self-aggregates in a calcium-independent fashion, and is believed to have strong tendencies to aggregate with cell membranes, should be used in combination with non-aggregating phospholipids. Phosphatidyl ethanolamine is commercially available, isolated from egg, bacteria, bovine, or plasmalogen or as the synthetic dioctadecanoyl, dioleoyl, dihexadecyl, dilauryl, dimyristoyl and dipalmitoyl derivatives.

Steroids

Steroids such as cholesterol (a natural constituent of membranes), estrogens (such as estriol, estrone, estradiol and diethylstilbestrol), and androgens (such as androstenedione and testosterone) cannot function alone as the liposphere coating but may be incorporated into the phospholipid surface coating, as well as serve as the core material.

Amphiphiles

Amphiphiles can be added to the phospholipid coating to alter the surface charge on the liposphere. Examples of amphiphiles that produce a positive charge on the coating are protonated long chain alkyl amines such as stearylamine or the corresponding secondary, tertiary or quaternary substituted amines. Examples of amphiphiles that produce a negative charge are arachidonic acid and other fatty acids.

Surfactants

The phospholipids can be substituted in part with surfactants such as Tween TM (a hydrophilic class of surfactants), Span TM (a hydrophobic class of surfactants), and polyethylene glycol surfactants.

Selection of Anesthetic

The anesthetic is any compound that is capable of blocking nerve impulses from the area of discomfort to the brain. In a preferred embodiment, the anesthetic is a local anesthetic such as marcaine, procaine (novocaine), chloroprocaine (nesacaine), cocaine, lidocaine, tetracaine (amethocaine, pontocaine), mepivacaine, etidocaine (duranest), bupivacaine (marcaine), dibucaine (cinchocaine, nupercaine), prilocaine (citanest), benzoxinate (dorsacaine), proparacaine (alcaine, opthaine, ophthetic), benzocaine (anesthesin), or butamben (butesin).

In an alternative embodiment, a general anesthetic that acts by blocking nerve conduction can be used in the liposphere, for example, one of the halocarbon anesthetics such as halothane, isoflurane, enflurane, or methoxyflurane. Centrally acting narcotics are not suitable for the preparation of liposperes with local anesthetic activity because they cause a loss of consciousness.

The choice of anesthetic will depend on the type of discomfort to be alleviated and is generally known to those skilled in the art of anesthesia. For example, procaine is commonly injected during dental procedures. Some local anesthetics are too toxic to be given by injection, and are restricted to topical applications to the skin, eye, or mucous membranes. Benoxinate and proparacaine are both commonly applied ophthalmic anesthetics. Cyclomethylcaine is used on damaged or diseased skin and on the mucosa of the rectum and the genitourinary system. Dimethisquin is used as an antipruritic for the relief of itching and pain associated with dermal lesions. Dyclonine, hexylcaine, and pramoxine, are also used to relieve dermal discomfort.

Melt preparation of Liposperes

In the preferred embodiment, liposperes are prepared by: (1) melting the anesthetic, or dissolving or dispersing the anesthetic in a liquid vehicle to form a liquid anesthetic which can be solidified by decreasing temperature; (2) adding phospholipid followed by an aqueous medium to the liquid anesthetic at a temperature higher than the melting temperature of the liquid anesthetic to form a suspension of the anesthetic; (3) mixing the suspension at a temperature above the melting temperature of the liquid anesthetic until a homogeneous fine preparation is obtained; and then (4) rapidly cooling the preparation to below the melting temperature to solidify the liquid core.

Suitable methods of mixing the suspension include mechanical shaking or stirring, fine mixing using homogenizing and sonication.

Solvent Preparation of Liposperes

Alternatively, liposperes can be prepared by solvent processing. In this method of preparation of liposperes involves the use of a rotovaporizer containing glass beads. The anesthetic, carrier, and phospholipid in an organic solvent are added to the rotovaporizer with beads. The solvent is then evaporated, and the resulting solid is mixed with an appropriate amount of buffer and rotation continued until a homogeneous mixture is obtained (for example, for another thirty minutes). The temperature is then reduced to 10° C. with continuation rotation for approximately five minutes to form a milky suspension of liposperes.

In an aqueous solution, the liposperes form a uniform fine dispersion of microspheres coated with a layer of a phospholipid, with the hydrophobic side of the phospholipid embedded in the outermost layer of the solid hydrophobic core and the hydrophilic side at the aqueous interface. The particle size, particle distribution, and phospholipid coating can be altered by varying the concentration and properties of the solid vehicle, the lipid, and the mixing method. For intravenous injections, particles should be less than five microns. For subdermal or intramuscular injections, the particle is preferably less than 250 $\mu$ in diameter. Larger particle sizes can be used for oral formulations. For controlled drug delivery, the average particle size of the liposphere should be greater than one micron.

A preferred range of anesthetic to carrier to phospholipid is from 1:0:0.01 to 1:100:100. Other biologically active materials can also be encapsulated in the lipospheres during either melt preparation or solvent preparation, in addition to, or in place of the anesthetics. Examples of biologically active materials include drugs (anti-inflammatories, anesthetics, antimicrobials, neuroactive agents, nutritional supplements, etc.) as well as applications for non-pharmaceutical uses, including pesticides, insect repellants, cosmetics, and fertilizers.

The method of preparation of lipospheres described herein is simple and is characterized by high loading, reproducibility, versatility, and stability. The method is further illustrated by the following non-limiting examples.

EXAMPLE 1

Method of Preparation of Lidocaine Liposphere with Tristearin Carrier

To a 20 ml vial was added lidocaine (100 mg), tristearin (500 mg), and L-α-lecithin (200 mg). The vial was heated to 65° C. to melt the tristearin and dissolve the lidocaine. 0.1M phosphate buffer pH 7.4 (60°-70° C., 10 ml; final concentration of lidocaine: 10 mg/ml) was added and the formulation mixed well by vigorous hand shaking and by vortexing for about five minutes. The uniform milk-like formulation (pH 8.3) was immediately cooled to room temperature by immersing the vial in a dry ice-acetone bath with continued shaking. The pH was adjusted to 7.4 with 1N HCl.

The drug concentration in the inner core of the resulting lipospheres was 9.5 mg/ml (95% yield), as determined by UV absorption (at 240 and 260 nm) of 100 microliters of the formulation dissolved in 2 ml of an ethanol:dichloromethane mixture.

The particle size was determined in three ways. Particle sizes of less than 10 micron were determined using a Coulter Particle Analyzer. Particle size of greater than 10 microns were determined by passing the formulation through a set of sieves in the range of 200 to 38 microns and weighing the particles remaining on each screen after drying. The shape and size was verified by examining the samples under a microscope.

The particles were spherical in shape with an average particle size of approximately 40 microns. The distribution of the particle sizes was >200 μ, <1%; 106-200 μ, 12%; 68-106 μ, 8%; 38-68 μ, 5%; 1-38 μ, 67%; and <1 μ, 7%.

Similar results were obtained when 1 gram of tristearin or 0.4 gram of L-α-lecithin was used.

EXAMPLE 2

Preparation of Marcaine Liposphere with Ethyl Stearate Carrier

In a scintillation vial, 100 mg of marcaine was mixed with 400 mg of ethyl stearate. Phosphatidyl choline, PC, (200 mg), from egg yolk or soybean, was spread as a thin film on the side of the scintillation vial. The vial was heated to 60° C., with continuous vortexing, to insure a uniform solid solution. Phosphate buffer solution (45°-50° C., 10 ml) was added and the formulation was thoroughly mixed by vortexing. The formulation was immediately brought to room temperature by intermittently dipping the vial in a dry ice-acetone bath with continuous shaking. The formulation was milky in appearance.

The average particle size of the above formulation was 15 microns, as determined by a Coulter Particle Size Analyzer.

EXAMPLE 3

Preparation of Marcaine Hydrochloride Liposphere with Ethyl Stearate Carrier

Lipospheres were made as in Example 2 except that marcaine hydrochloride was used in place of marcaine. The particle size of this formulation was dependent on the initial particle size of the marcaine hydrochloride because it does not melt at the temperature of preparation.

EXAMPLE 4

Preparation of Marcaine Liposphere with Tristearin as Carrier

Lipospheres were made as in Example 2 except that ethyl stearate was substituted with tristearin. The contents of the vial were heated to 65° C. The buffer was heated to 70° C. before adding to the solid solution. The lipospheres were spherical in shape and the formulation was milky in appearance.

EXAMPLE 5

Comparison of Lipospheres with Different Concentrations of Marcaine

Marcaine lipospheres were prepared according to the method described in Example 2, with different ratios of anesthetic to carrier to phospholipid.

In the first group, the amount of marcaine was varied from 50 mg to 800 mg. The amount of tristearin and phosphatidyl choline remained constant at 400 mg and 200 mg, respectively. In the second group, the amounts of marcaine and phosphatidyl choline were kept constant at 100 mg and 200 mg, respectively, and the amount of tristearin was varied from 50 mg to 800 mg. In the third group, the amounts of marcaine and tristearin were kept constant and the concentration of phosphatidyl choline was varied from 5 to 50 mg/ml.

All of the above liposphere formulations were very uniform and milky in appearance. There was no significant difference between the average particle size of these formulations and the lipospheres described in Example 4.

EXAMPLE 6

Preparation of Marcaine Lipospheres with Different Carriers

Several liposphere formulations were prepared with marcaine:carrier:phosphatidyl choline in a ratio of 1:4:2. The carriers used were tripalmitin (99%), trilaurin, trimyristin, tricaprin and the mixed triglycerides of tristearin and tripalmitin in the ratio of 70:30. The formulations were milky in appearance and had an average particle size of about 15 microns.

EXAMPLE 7

Stability of Lipospheres

The stability of the particle size and the distribution of the liposphere formulations prepared in examples two through six were evaluated by storing the formulations at room temperature and 4° C. The particle sizes and distributions were similar to the original formulation after 30 days. Lipospheres of lidocaine prepared with tristearin as the carrier were stable for ten months at 4° C., and showed no signs of aggregation.

EXAMPLE 8

In Vitro Release Rates from Liposphere Formulations

In vitro release experiments were conducted in dialysis tubing with a molecular weight cut off of 300,000. One milliliter of liposheres prepared from tristearin and phosphatidyl choline (marcaine:tristearin:phosphatidyl choline, 1:4:2; marcaine:tristearin:phosphatidyl choline, 2:4:2; marcaine:tristearin:phosphatidyl choline, 4:4:2) and marcaine hydrochloride was placed in a pre-washed dialysis tubing. The clamped dialysis tubing was placed in a jar containing 800 ml of buffer. The jars were placed on an orbital shaker at 100 rpm, in an oven equilibrated at 37° C. Samples were taken at discrete times and analyzed by HPLC to determine the release kinetics of marcaine from the liposphere formulation. As a control, a solution of marcaine hydrochloride was placed in a dialysis tubing to determine if the dialysis tubing was limiting the rate of release.

Representative release profiles are shown in FIG. 1. There is an initial burst of anesthetic released in the first few hours, followed by a sustained release for at least three to four days.

EXAMPLE 9

In Vivo Anesthetic Activity of Marcaine Liposheres

A. Effect of concentration of Marcaine

Liposphere containing either effective concentrations of 10 (Composition A) or 40 mg (Composition B) marcaine were tested in vivo for their local anesthetic activity. Both formulations were prepared as described in Example 4. Composition A was prepared from 1:4:1 marcaine:tristearin:phosphatidyl choline (1:4:1), and composition B was prepared from marcaine:tristearin:-phosphatidyl choline (4:4:2).

Male Sprague-Dawley rats (250-300 grams) were used for all studies. A 20% (w:v) suspension of brewer's yeast was made in distilled water. Prior to injection, pain threshold was determined in each animal using a Randall-Sellito apparatus (Stoelting Company, Chicago). This was accomplished by placing the left rear foot on the teflon pad, and applying force to the dorsal surface of the paw at a constant linear rate by means of a second teflon pad. The mass applied to the paw was indicated on a scale. The applied mass at which the animal withdrew its paw was recorded.

To induce hyperalgesia, animals were anesthetized with 5% isoflurane in air. Then 100 μl of the 20% yeast solution was injected after inserting a ⅜ inch 25 g needle through the pad nearest the first digit, in the direction of the center of the foot, to a depth of 6 mm. Animals were immediately returned to their cages, where they recovered from the anesthesia within 3 to 5 minutes. The foot withdrawal score was then measured at the indicated times after the injection, on a scale from 0 to 25 (0 = could not stand any pressure; 25=could stand extensive pressure). Liposheres to be tested were co-administered with the yeast solution. Control animals received an identical volume of water. If animals were to be tested more than 24 hours after the administration of liposheres, then the liposphere solution was injected at time 0 and yeast was injected 24 hours before the measurement was to be made, since yeast-induced hyperalgesia is often not measurable at times greater than 24 hours after administration.

The results are shown in Table 1. The numbers indicate the amount of pressure that the rats could withstand before withdrawing their paws. A test withdrawal value higher than the value measured for yeast alone indicates that the paw is anesthetized. The results demonstrate that the liposheres effectively release marcaine for at least 48 hours.

TABLE 1

| | Effectiveness of Marcaine Liposheres on Suppressing Pain | | | | |
|---|---|---|---|---|---|
| | Time, Hours | | | | |
| | 0 | 1 | 6 | 24 | 48 |
| Yeast | 5.3 ± 0.3 | 4.6 ± 0.3 | 2.5 ± 0.3 | 2.6 ± 0.4 | 2.3 ± 0.2 |
| Composition A | 5.4 ± 0.3 | 25 ± 0 | 8.2 ± 2.1 | 5.4 ± 0.5 | 4.6 ± 0.2 |
| Composition B | 5.6 ± 4 | 25 ± 0 | 11.4 ± 1.5 | 4.9 ± 0.5 | 5.0 ± 0.3 |

B. Effect of Carrier

In another in vivo experiment, two different carriers were compared. Formulation A contained marcaine:ethyl stearate:phosphatidyl choline in the ratio of 1:4:2. Formulation B had the same composition except that ethyl stearate was replaced with tristearin. The concentration of marcaine in the final formulation was 10 mg/ml. The results provided in Table 2 demonstrate that marcaine is effectively released for at least 72 hours and that greater release is achieved with ethyl stearate than tristearin.

TABLE 2

| | Effectiveness of Marcaine Liposheres on Suppressing Pain | | | | |
|---|---|---|---|---|---|
| | Time, Hours | | | | |
| | 0 | 6 | 24 | 48 | 72 |
| Carrageenan | 8.2 ± 0.3 | 4.1 ± 0.04 | 4.1 ± 0.04 | 4.1 ± 0.04 | 4.1 ± 0.04 |
| Formulation A | 7.9 ± 1.2 | 8.4 ± 1.9 | 4.4 ± 2.9 | 10.7 ± 1.4 | 9.9 ± 2.8 |
| Formulation B | 7.8 ± 1.2 | 10.7 ± 1.1 | 7.1 ± 0.7 | 5.6 ± 0.8 | 5.5 ± 0.8 |

In another in vivo experiment, the effect of varying the concentration of anesthetic in the liposphere formulation was again evaluated. Several different formulations were prepared as described in Table 3. All of the formulations were prepared as described in Example 3, using 10 ml of buffer.

TABLE 3

| | Marcaine Liposphere Composition | | |
|---|---|---|---|
| Formulation | Marcaine (mgs) | Tristearin (mgs) | PCS (mgs) |
| A | 100 | 400 | 200 |
| B | 200 | 400 | 200 |
| C | 400 | 400 | 200 |
| D | 600 | 400 | 200 |
| E | 400 | 400 | 400 |

The in vivo anesthesia provided by the above formulations, tested using the method described in Example 9, is described in Table 4.

TABLE 4

| | Effectiveness of Marcaine Liposheres in Suppressing Pain | | | | |
|---|---|---|---|---|---|
| | Time, Hours | | | | |
| | 0 | 1 | 6 | 24 | 48 |
| Yeast | 4.9 ± 0.3 | 4.6 ± 0.3 | 3.1 ± 0.3 | 2.1 ± 0.4 | 2.4 ± 0.2 |
| A | 4.9 ± 0.3 | 17 ± 2.2 | 8.3 ± 0.8 | 5.3 ± 0.3 | 5.2 ± 0.2 |
| B | 4.8 ± 0.5 | 24.2 ± 0.6 | 11.3 ± 1.8 | 8.0 ± 0.6 | 5.5 ± 0.4 |

TABLE 4-continued

| | Effectiveness of Marcaine Liposphres in Suppressing Pain | | | | |
|---|---|---|---|---|---|
| | Time, Hours | | | | |
| | 0 | 1 | 6 | 24 | 48 |
| C | 5.2 ± 0.2 | 24 ± 0.2 | 19.2 ± 1.9 | 12.3 ± 2.1 | 11.8 ± 2.0 |
| D | 5.2 ± 0.8 | 25 ± 0.0 | 20.6 ± 1.8 | 15.4 ± 1.5 | 13.8 ± 2.0 |
| E | 5.8 ± 0.4 | 25 ± 0.0 | 21.4 ± 1.3 | 13.6 ± 1.6 | 8.9 ± 0.7 |

Figure 2:
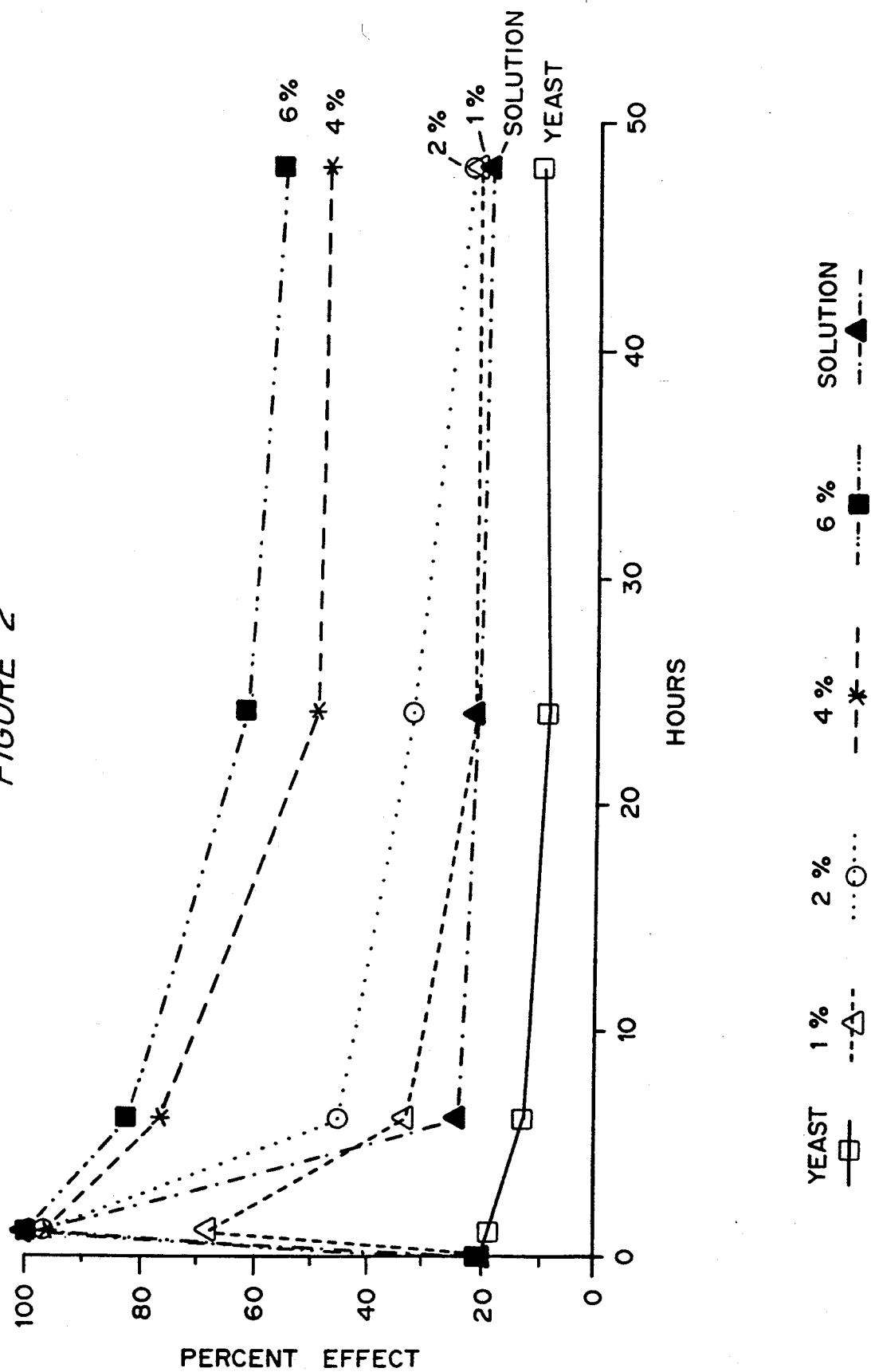
FIG. 2 is a graph of the in vivo percent effect over time (hours) of marcaine from liposphere having loadings of 1% (-triangle-), 2% (-O-), 4% (-*-), and 6% (-dark square-), compared with a yeast control (-square-) and 1% marcaine HCl solution (-dark triangle-).

The results of Table 4 are shown graphically in FIG. 2 as percent effect, where 25 units equals 100%.

EXAMPLE 10

Preparation of Liposphres by Sonication

Marcaine was mixed with tristearin in a scintillation vial. The vial was coated with phosphatidyl choline (final formulations of marcaine:tristearin:PCS of 1:4:2 and 1:4:1, corresponding to formulations A and B in Table 4). The vial was heated to 65° C. and vortexed for 2 minutes to ensure proper mixing of the two ingredients. To that mixture was then added 10 ml of hot phosphate buffer. The mixture was sonicated for ten minutes with intermittent cooling until it came to room temperature. The liposphres were less viscous than liposphres made by the vortex method (Example 2). The average particle size obtained was six microns.

The formulations were tested in vivo for their ability to decrease sensitivity in the rat paw, by the method described in Example 9 above. The results are provided in Table 5.

TABLE 5

| | Effectiveness of Marcaine Liposphres in Suppressing Pain | | | | |
|---|---|---|---|---|---|
| | Time, Hours | | | | |
| | 0 | 1 | 6 | 24 | 48 |
| Yeast | 5.8 ± 0.4 | 5.3 ± 0.3 | 3.7 ± 0.5 | 2.4 ± 0.3 | 2.7 ± 0.2 |
| Formulation A | 6.0 ± 0.4 | 9.5 ± 0.9 | 8.1 ± 1.0 | 7.1 ± 0.5 | 6.2 ± 0.5 |
| Formulation B | 5.8 ± 0.5 | 12.2 ± 1.4 | 5.7 ± 0.4 | 4.6 ± 0.4 | 3.1 ± 0.4 |

EXAMPLE 11

Preparation of Liposphres by Rotoevaporation

To a round bottom flask containing 100 grams of glass beads (3 mm in diameter), 50 ml of chloroform was added. To that 1 gm of phosphatidyl choline, 1 gm of tristearin and 200 mg of marcaine was added and mixed thoroughly till a clear solution was obtained. The chloroform was evaporated using a rotoevaporizer under reduced temperature at room temperature. The temperature was raised to 40° C. after 20 minutes to ensure complete removal of chloroform. A thin film of solids was obtained around the round bottom flask and the glass beads. Ten milliliters of 0.9% saline was added to the round bottom flask and the contents were mixed for 30 minutes at room temperature. At the end of thirty minutes, the temperature was lowered to 10° C. by placing in crushed ice and mixing was continued for another half hour. The liposphres formed were spherical in shape and the average particle size was three to five microns.

Liposphres of polylactic acid (molecular weight 2,000) were prepared similarly using weight ratio of marcaine:polylactic acid:phosphatidyl choline of 1:4:2. A nice, uniform suspension of liposphres, having an average diameter of approximately 39 microns, was obtained.

The rate of release of anesthetic from liposphres prepared as in Example 11 is very similar to the release from liposphres prepared by vortexing (Example 2). However, the average particle size of liposphre using the method of Example 11 is approximately eight to ten microns and there is a very narrow particle size distribution, whereas the average particle size and distribution of liposphres prepared by the vortexing method is 15 to 30 microns.

EXAMPLE 12

Preparation of Marcaine Liposphres by Sonication

A thin film of the mixture of marcaine, tristearin and phosphatidyl choline was prepared in a round bottom flask as described in Example 10. Ten milliliters of isotonic phosphate buffer, pH 7.4 was added to the round bottom flask. An ultrasound probe was inserted into the round bottom flask and the contents were sonicated for 20 minutes at room temperature. The resulting liposphres were spherical in shape and the average particle size was less than a micron. The liposphres were exceptionally stable as determined by the particle size analyzer after seven days. The release of marcaine from liposphres made by sonication is also shown in FIG. 1.

EXAMPLE 13

Effect of Gamma Radiation Sterilization on Marcaine Liposphres

Marcaine liposphres were prepared with ratios of marcaine:tristearin:phosphatidyl choline (1:4:1 and 2:4:2).

These liposphres were sent to Isomedix, Inc. (7828 Nagie Avenue, Mountain Grove, Ill., 60053) for gamma irradiation to sterilize the liposphres. The samples were irradiated for 575 minutes. The maximum dose delivered was 2.33 Mrads. The irradiated samples were analyzed for the particle size distribution, in vitro release characteristics and the in vivo activity.

The average particle size of the irradiated sample was 44 microns. This is not substantially different from the average particle size of samples stored for two weeks at 0° C. (or −20° C.) in the freezer. The kinetics of release of marcaine from the liposphres before and after gamma irradiation are provided in FIG. 1, along with the data for the release of marcaine from liposphres prepared as in Example 8.

EXAMPLE 14

Treatment or Preparation of Liposphres with

Marcaine liposphres prepared as described in Example 2 had a standard size deviation of 16.90 microns. These liposphres were pumped into a microfluidizer to refine the particle size. The microfluidizer does not change the particle size but does narrow the particle size distribution. The standard deviation decreased to 10.79 microns after 8 passes and to 9.43 microns after 40 passes. The skewness also decreased considerably. A similar phenomenon was observed when the liposphres were prepared using a homogenizer.

Liposphres can also be prepared with a microfluidizer that is equipped with two separate entry ports. The entire equipment is thermally jacketed. Through one entry port, a homogenous melt solution or suspension of drug and carrier is pumped. Through the other port is pumped an aqueous buffer. The two liquids are mixed in the instrument at elevated temperatures where the carrier is melted and rapidly cooled to form the liposphere. The temperature of the microfluidizer can be changed at any stage of the liposphere processing to manipulate the particle size and distribution.

EXAMPLE 15

Sterilization of Liposheres by Filtration of Lipospheres or Components

A. Sterilization by filtration

In a scintillation vial, 100 mg of marcaine was mixed with 400 mg of ethyl stearate. Phosphatidyl choline, PCS, (200 mg), from egg yolk or soybean, was spread as a thin film on the side of the scintillation vial. The vial was heated to 60° C., with continuous vortexing, to ensure a uniform solid solution. Hot buffer solution (45°-50° C., 10 ml) was added and the formulation was thoroughly mixed by vortex. The formulation was filtered through a 0.2 micron membrane filter, using a preheated sterile syringe, into a sterile scintillation vial. The vial was immediately brought to room temperature by intermittently dipping the vial in a dry ice-acetone bath with continuous shaking. The formulation was milky in appearance. The average particle size of this formulation was 15 microns, as determined by LS100 Coulter Particle Size Analyzer.

B. Sterilization by using presterilized ingredients

The ingredients are sterilized separately using dry or moist heat, and the final formulation then sterilized with ultra violet radiation. Alternatively, the presterilized ingredients are aseptically processed to obtain sterile liposheres.

For example, liposheres were sterilized by filtering the components through 0.2 μ filters. The liposheres were prepared by dissolving 20 g maracine, 20 g phosphatidyl choline, 1.25 g methyl parabens (0.12%) and 0.5 g propyl parabens (0.05%) in 100% ethanol, filtering, adding 40 g tristearin dissolved in 400 ml boiling 100% ethanol that had also been filtered, and mixing in a one liter round bottom flask. The Mixture was evaporated to dryness by rotoevaporation in a 70° C. water bath. 0.1M phosphate buffer pH 7.4 was added to the dry material up to one liter, then the mixture homogenized five minutes at maximum speed at 70° C., then in dry ice-acetone for another five minutes. The resulting liposheres were packaged in ten ml vials, stoppered and stored at either 4° C. or in the freezer. The average particle diameter was 7.8 μ.

EXAMPLE 6

Method of Preparation of Lidocaine Liposhere without Vehicle

To a 20 ml vial was added lidocaine (600 mg) and L-α-olecithin (125 mg from egg yolk). The vial was heated to 70° C. to melt the lidocaine and then hot buffer solution (60°-70° C., 5 ml) was added. The formulation was mixed well by vigorous hand shaking and by vortexing for about 5 minutes. The uniform milky-appearing formulation was immediately cooled to room temperature by immersing the vial in a dry ice-acetone bath with continued shaking.

The resulting liposheres had a lidocaine concentration of 125 mg/ml (100% yield). The particle size ranged from 0.35 ±0.176 microns. The average particle size was 12.63 microns as determined by an LS 100 coulter particle size analyzer. The formulation was effective for 24 hours when tested in the rat paw carrageenan model (Example 9).

EXAMPLE 7

Reconstitution of Lyophilized Liposhere Formulations

Liposhere formulations prepared as described above were lyophilized to dryness to form a sticky fluffy cake. The cake weight varied according to the amount of solids added. Reconstitution of the cakes by addition of sterile water (3 ml) followed by vortexing for one minute resulted in formulations with drug concentration and particle size similar to the original formulation.

EXAMPLE 8

Liposheres Containing Local Anesthetics for Severe Pain

Liposhere formulations, containing 5% and 10% marcaine. Sustained release were prepared from marcaine:tristearin:egg yolk phosphatidyl choline in a ratio of 5:4:2 and 10:4:2. The formulations were uniform, white, and creamy. The liposheres were tested for their ability to moderate acute and chronic pain. The liposheres, either in the form of a viscous liquid, gel or solid matrix, were inserted along the sciatic nerve in rats anesthetized with methohexital, chosen for short duration and lack of residual analgesia. Motor block was tested by a standardized scoring procedure when the animals were ambulating. Sensory block was tested via several methods including vocalization threshold to calibrated electrical stimulation via transcutaneous electrodes on the lateral aspect of the foot. Contralateral testing and testing in the saphenous nerve dermatomes were used as controls. Control animals received liposheres without local anesthetics or sham dissection. In all groups, ipsilateral and contralateral dorsal root ganglia and spinal cord were removed for molecular biology studies as described above. At the end of the study, sciatic nerves were studied in two ways: (1) electrophysiology to confirm reversibility of blockade following washing after removal of the liposheres, and (2) histopathologic studies of the sciatic nerve to look for signs of injury.

A similar dose of anesthetic in solution would have killed the animals. However, with the liposhere formulation the anesthetic activity remained localized with no systemic effects. Both formulations showed a high degree of motor and sensory block for four days, with better activity at days three and four for the 10% formulation.

The nerve returned to normal after the study with no injury or inflammation as determined by electrophysiology and histopathologic examinations. This study demonstrates the potential use of liposhere-local anesthetics for the management of severe pain, such as intracostal pain.

Modifications and variations of the present invention, liposhere delivery systems for anesthetics, will be obvious to those skilled in the art from the foregoing detailed description. Such modifications and variations are intended to come within the scope of the appended claims.

We claim:

1. A liposhere comprising:

a core formed of a hydrophobic material existing as a solid at a temperature of 30° C. having anesthetic activity as a result of an anesthetic compound, and a phospholipid coating surrounding the core, wherein the hydrophobic ends of the phospholipid are embedded in the solid core and the hydrophilic ends of the phospholipid are exposed on the surface of the liposphere, the combination forming a spherical structure having an average particle diameter between 0.35 and 250 microns, wherein the core may contain a vehicle for the anesthetic compound, and the anesthetic compound, vehicle, and phospholipid coating are in a ratio of anesthetic compound to vehicle to phospholipid between 1:0:0.01 and 1:100:100.

2. The liposphere of claim 1, wherein the anesthetic activity is produced by a local anesthetic compound.

3. The liposphere of claim 2 wherein the local anesthetic is selected from the group consisting of marcaine, procaine, chloroprocaine, cocaine, lidocaine, tetracaine, mepivacaine, etidocaine, bupivacaine, dibucaine, prilocaine, benzoxinate, proparacaine, benzocaine, butamben, and combinations thereof.

4. The liposphere of claim 1 wherein the solid core comprises an anesthetic compound in a solid inert vehicle.

5. The liposphere of claim 1 wherein the solid core has a melting point between 30° C. and 120° C.

6. The liposphere of claim 4 wherein the vehicle is selected from the group consisting of natural and synthetic waxes, fatty acid esters, fatty alcohols, solid hydrogenated plant oils, tristearin, and biodegradable natural and synthetic polymers.

7. The liposphere of claim 1 wherein the anesthetic activity is produced by a compound selected from the group consisting of halothane, isoflurane, enflurane, and methoxyflurane.

8. The liposphere of claim 1 in a pharmaceutically acceptable carrier for enteral administration to a patient.

9. The liposphere of claim 1 wherein the liposphere is in a pharmaceutically acceptable carrier for topical administration to a patient.

10. The liposphere of claim 1 in a pharmaceutically acceptable carrier for parenteral administration to a patient.

11. The liposphere of claim 1, further comprising a preservative.

12. The liposphere of claim 1 further comprising a pharmaceutically active agent selected from the group consisting of antibiotics, antifungals, antivirals, chemotherapeutic agents and combinations thereof.

13. A method of inducing local anesthesia comprising administering to a patient lipospheres comprising:

a core formed of a hydrophobic material existing as a solid at 30° C. having anesthetic activity as a result of an anesthetic compound, and a phospholipid coating surrounding the core, wherein the hydrophobic ends of the phospholipid are embedded in the solid core and the hydrophilic ends of the phospholipid are exposed on the surface of the liposphere, the combination forming a spherical structure having an average particle diameter between 0.35 and 250 microns, wherein the core may contain a vehicle for the anesthetic compound, and the anesthetic compound, vehicle, and phospholipid coating are in a ratio of anesthetic compound to vehicle to phospholipid between 1:0:0.01 and 1:100:100 in a pharmaceutically acceptable carrier.

14. The method of claim 13 wherein the anesthetic activity is produced by a local anesthetic compound.

15. The method of claim 14 wherein the local anesthetic is selected from the group consisting marcaine, procaine, chloroprocaine, cocaine, lidocaine, tetracaine, mepivacaine, etidocaine, bupivacaine, dibucaine, prilocaine, benzoxinate, proparacaine, benzocaine, or butamben.

16. The method of claim 13 wherein the solid core includes an anesthetic compound and a vehicle for the anesthetic compound, which in combination with the anesthetic compound exists as a solid at 30° C.

17. The method of claim 13 wherein the solid core has a melting point between 30° C. and 120° C.

18. The method of claim 16 wherein the vehicle is selected from the group consisting of natural and synthetic waxes, fatty acid esters, fatty alcohols, solid hydrogenated castor and vegetable oils, tristearin, and biodegradable polymer.

19. The method of claim 13 wherein the anesthetic activity is produced by a compound selected from the group consisting of halothane, isoflurane, enflurane, and methoxyflurane.

20. The method of claim 13 wherein the liposphere is administered parenterally to the patient.

21. The method of claim 13 wherein the liposphere is administered topically in a pharmaceutically acceptable carrier for topical administration.

22. The method of claim 13 wherein the liposphere is administered enterally to the patient.

23. The method of claim 13, wherein the core further comprises a preservative.

24. The method of claim 13 further comprising a pharmaceutically active agent selected from the group consisting of antibiotics, antifungals, antivirals, chemotherapeutic agents and combinations thereof.

25. A method of making liposhperes formed of a core that is a hydrophobic material existing as a solid at a temperature of 30° C. and a phospholipid coating surrounding the core, wherein the hydrophobic ends of the phospholipid are embedded in the solid core and the hydrophilic ends of the phospholipid are exposed on the surface of the resulting spherical liposphere structure having an average particle diameter between 0.35 and 250 microns, comprising forming a liquid of the hydrophobic core material, adding phospholipid to the core material, adding an aqueous solution to the liquid core material and phospholipid mixture, and mixing the liquid core material and phospholipid until a suspension of liposheres is formed.

26. The method of claim 25 further comprising sonicating and cooling the liquid core material and phospholipid after mixing.

27. The method of claim 25 wherein the liquid core material and phospholipid are heated during mixing to a temperature at which the core material melts.

28. The method of claim 25 wherein the the liquid core material includes an organic solvent, further comprising evaporating the solvent while mixing the core material and phospholipid.

29. The method of claim 28 wherein aqueous buffer is added to the core material-phospholipid mixture after evaporating the solvent and before mixing until a suspension of liposheres is formed.

* * * * *